United States Patent [19]

Sih

[11] Patent Number: 5,541,080
[45] Date of Patent: * Jul. 30, 1996

[54] METHOD FOR PREPARING L-ALPHA-AMINO ACIDS

[75] Inventor: Charles J. Sih, Madison, Wis.

[73] Assignee: Wisconsin Alumni Research Fdn., Madison, Wis.

[ * ] Notice: The term of this patent shall not extend beyond the expiration date of Pat. No. 5,219,731.

[21] Appl. No.: 69,277

[22] Filed: May 28, 1993

Related U.S. Application Data

[63] Continuation-in-part of Ser. No. 786,731, Nov. 1, 1991, Pat. No. 5,219,731.
[51] Int. Cl.$^6$ .............................. C12Q 1/34; C12Q 1/37; C07B 57/00
[52] U.S. Cl. .............................. 435/18; 435/24; 548/228; 548/232; 564/303
[58] Field of Search ..................... 435/18, 24; 548/215, 548/228, 232, 238, 239, 249; 564/303, 304

[56] References Cited

FOREIGN PATENT DOCUMENTS

| | | |
|---|---|---|
| 62-129238 | 6/1987 | Japan . |
| 2-215391 | 8/1990 | Japan . |
| 2-234685 | 9/1990 | Japan . |
| 9015146 | 12/1990 | WIPO . |

OTHER PUBLICATIONS

Sih et al., *J. Indus. Micro., Suppl.* 3, *Develop. Ind. Micro.*,29, 221–229 (1988).
Bevinakatti, H. S. et al., "Lipase–Catalyzed Enantioselective Ring–Opening of Oxagol–5(4H)–ones Coupled With Partial in Situ Rocemisation of the Less Reactive Isomer", *J. Chem. Soc. Comm.*, 1990, pp. 1091–1092.
McGahren et al., *Tetrahedron*, 23, 2017 (1967).
Chibata et al., *J. Appl. Microbiol.*, 13 638 (1965).
T. Fukumura, *Agric. Biol. Chem.*, 41 1321 and 1327 (1977).
de Jersey et al., *Biochemistry*, 8 1967 (1969).
Bautista, F. M., Porcine Pancreatic Lipase–Catalyzed Amino Acids (1992) 2:87–95.
O'Donnell, M. J. et al., "Steroselective Synthesis . . . ", *JACS* v. III:6, pp. 2353–2355, 1989.
Daffe, V. et al. "Enantiomeric Enrichment . . . ", *JACS* v. 102:10, pp. 3601–3604, 1980.

*Primary Examiner*—Ralph J. Gitomer
*Attorney, Agent, or Firm*—Andrus, Sceales, Starke & Sawall

[57] ABSTRACT

A process is provided for preparing an L-α-amino acid from a 5(4H)-oxazolone precursor. The precursor is subjected to a two-step process sequence in which the precursor is first contacted with a methanolytically active lipase in the presence of methanol in a non-polar solvent to enantioselectively solvolyze the precursor and produce an intermediate optically active methyl ester of the desired α-amino acid. This ester is then contacted with a protease in the presence of water to enantioselectively cleave the ester and accomplish an enzymatic kinetic resolution to prepare the product L-α-amino acid in high optical purity.

14 Claims, 1 Drawing Sheet

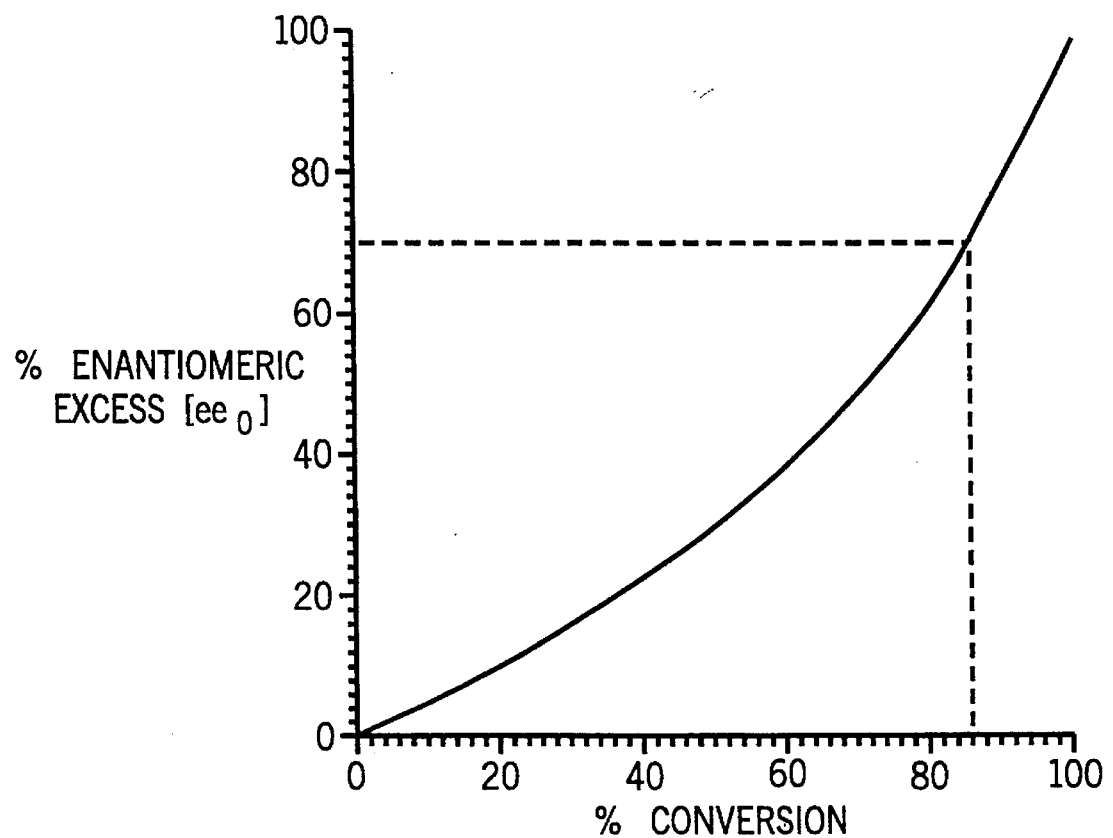

METHOD FOR PREPARING L-ALPHA-AMINO ACIDS

RELATED APPLICATION

This application is a continuation-in-part of application Ser. No. 786,731, filed Nov. 1, 1991 now U.S. Pat. No. 5,219,731.

FIELD OF THE INVENTION

This invention relates to the enzymatic preparation of L-α-amino acids of high optical purity from 5(4H)-oxazolone precursors by first contacting the precursor with a lipase and then with a protease under liquid phase conditions.

BACKGROUND OF THE INVENTION

Optically-active amino acids in high purity are becoming increasingly important as intermediates for the preparation of pharmaceuticals, food and agrochemicals. For example, some are side chain precursors for the semisynthetic penicillins, ampicillin and amoxycillin. Also, the most important building block for the low calorie sweetener, aspartame, is L-phenylalanine. D-valine, for instance, is an intermediate for the pyrethroid insecticide, Fluvalinate. In addition, D-phenylalanine possesses analgesic properties and might one day supplant aspirin. Further, there are numerous examples of essential optically active amino acids which are important in human nutrition.

For many applications, the particular optically active amino acid that is required as a starting material must have an optical purity of at least about 65% and preferably at least about 90%. Such a purity level appears to be a requirement particularly in the case of optically active acyl amino acids. Also, for reasons of commercial practicality, a particular required optically active amino acid needs to be made from a starting precursor in a yield that is economical. For example, a yield of at least about 50% of an amino acid enantiomer appears to be desirable.

Previously, I have provided a method for preparing optically-active amino acid derivatives involving the contacting of a hydrolytically active lipase in a solvent with an oxazolone precursor; in particular, a 5(4H)-oxazolone (see pending Ser. No. 786,731). This method produces amino acids in substantial enantiomeric excess.

Although very useful, this method has a reaction rate and degree of enantioselectivity that vary depending on the C-4 substituents present in the precursor 5(4H)-oxazolones. It would be desirable to have an improved enzyme catalyzed synthetic process for directly producing any one of many natural and non-natural L-amino acids in high optical purity, in high yield, and at a useful reaction rate from such precursors.

The present invention provides such an improved process.

SUMMARY OF THE INVENTION

The present invention relates to a sequential two-step enzymatic method for directly producing an optically-active amino acid, particularly an L-α-amino acid, in high optical purity, in high yields and at a useful reaction rate from a 5(4H)-oxazolone.

Characteristically, the resulting optically active L-α-amino acid product has an optical purity of at least about 90%. Also, this product is produced in a yield of at least about 50% (based on the oxazolone precursor). Thus, the product L-α-amino acids are produced at practical yields and typically are directly usable for many applications without an intervening purification procedure.

More specifically, in the inventive process, two successive enzymatic asymmetric reaction steps are carried out. In a first step, a selected 5(4H)-oxazolone amino acid precursor is cleaved in a non-polar organic liquid in the presence of both methanol as a nucleophile and a selected methanolytically active lipase as a catalyst. The precursor is enantioselectively solvolyzed, and an enantiomeric excess of the (S) form of an intermediate α-amino acid methyl ester is produced.

Then, in a second step, the methyl ester is cleaved under aqueous phase conditions in the presence of a selected hydrolytically active protease. Following the second cleaving procedure, an L-α-amino acid is recovered having an optical purity of at least about 90% in a yield greater than about 50% (based on the starting 5(4H)-oxazolone precursor). Both the first and second steps can be carried out in a relatively short time.

The inventive process provides a general procedure that is suitable for producing any one of many natural or non-natural L-α-amino acids in high optical purity (and high enantiomeric ratio), in high yield and at rapid reaction rates.

The inventive process is relatively simple, reliable and economical.

The inventive process is particularly well adapted for converting a wide variety of 4-substituted-2-substituted-oxazolin-5-one precursors to the corresponding optically-active N-substituted-L-α-amino acids. A preferred C-2 substituent in 5(4H)-oxazolone precursors is phenyl.

So far as now known, many of the various L-α-amino acids that can be produced according to the present invention have not previously been made synthetically by a single direct process in such high optical purity, in such high yields and at such high reaction rates. Thus, these products can be produced in a practical manner and used without further processing. No single enzymatic process has previously been available, so far as now known, by which so many L-α-amino acids could be produced at relatively rapid reaction rates and in such high optical purity and yields.

These and other objects, aims, purposes, features, benefits, advantages, embodiments, variations and the like will be apparent to those skilled in the art from the present specification taken with the accompanying drawings.

BRIEF DESCRIPTION OF THE DRAWING

In the drawings:

The FIGURE is a plot relating the initial percent enantiomeric excess (ee) to the percent conversion (c), with the final percent enantiomeric excess (ee') being fixed at 98% for the enzyme and with an enantiomeric ratio (E) being 100.

DETAILED DESCRIPTION (a) Definitions

As used herein, the term "enantioselectivity", or the symbol "E", refers to the selective capacity of an enzyme to generate from a racemic substrate one enantiomer relative to the other in a product racemic mixture. The enantioselectivity is quantitatively expressed by the formula:

$$E = \frac{\ln\left[1 - C\left(\frac{1+ee'}{1+ee^o}\right)\right]}{\ln\left[1 - C\left(\frac{1+ee'}{1-ee_o}\right)\right]} \quad (1)$$

wherein:

C is the extent of substrate conversion for the enzyme catalyzed product, $ee_o$ is the enantiomeric excess of one enantiomer relative to the other in a racemic mixture of an (R)-type and a corresponding (S)-type structure at the beginning of an enzymatic conversion of a substrate, and ee' is the enantiomeric excess at the termination of the enzymatic conversion.

For a starting racemic mixture containing equal amounts of the R and S enantiomer types, $ee_o$ is zero.

As used herein, the term "enantiomeric excess", or the symbol "<u>ee</u>", refers to the amount or excess of one enantiomer (whether (R)- or (S)-type) relative to the other in a racemic mixture of such enantiomers. This excess <u>ee</u> is quantitatively expressed by the formula:

$$\underline{ee} = \frac{R-S}{R+S} \quad (2)$$

where:

R is the molar concentration of the (R)-type enantiomer, and

S is the molar concentration of the (S)-type enantiomer.

As used herein, the term "optical purity" or the symbol "[α]", refers to the percent excess of one enantiomer over the other in a racemic mixture of an (R)-type and a corresponding (S)-type structure. This percent excess is expressed by the formula:

$$[\alpha] = \frac{R-S}{R+S}(100) \quad (3)$$

where:

R is the molar concentration of one enantiomer and
S is the molar concentration of the other enantiomer.

As used herein, the term "yield" refers to the quantity of a designated product resulting from the enzymatically catalyzed conversion of a substrate to the product expressed as a weight percent.

(a) Solvolysis

In the two-step procedure of the process of this invention, the first step is an enzymatic asymmetric solvolysis procedure.

In this solvolysis procedure, a dissolved oxazolone compound is contacted with methanol and a dissolved methanolytically active lipase enzyme in a non-polar solvent.

Various 5(4H)-oxazolones are preferred for use as starting materials (i.e., precursors or substrates) in the practice of this invention. Such precursors are racemic mixtures.

Presently more preferred substrate 5(4H)-oxazolones are 4-substituted-2-substituted-oxazolin-5-ones such as are characterized by the following generic racemate formula:

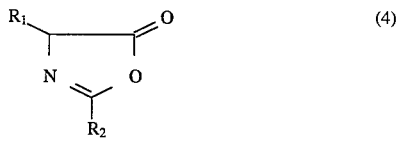

(4)

where $R_1$ and $R_2$ are each a monovalent organo moiety that is substantially inert in the presence of lipases and proteases.

Thus, in the practice of the process of this invention, $R_1$ and $R_2$ in a Formula (4) precursor are substantially inert towards the methanolytically active Pseudomonas lipases under the non-polar organic liquid contacting conditions described herein. Similarly, $R_1$ and $R_2$ in a Formula (5) precursor (as defined below) are also substantially inert towards the hydrolytically active proteases prozyme 6 and protease 2A under the aqueous liquid phase contacting conditions as described herein.

In Formula (4) compounds, $R_1$ and $R_2$ are preferably each independently selected from the group of monovalent radicals consisting of:

(a) aryl of 6 through 12 carbon atoms (phenyl being presently more preferred);

(b) alkaryl of 6 through 18 carbon atoms (tolyl and xylyl being presently more preferred);

(c) aralkylene of 7 through 18 carbon atoms (benzyl being presently more preferred);

(d) aralkenylene of 8 through 18 carbon atoms (phenylethenylene being presently more preferred);

(e) alkyl of less than 18 carbon atoms (lower alkyl being presently more preferred);

(f) alkenyl of less than 18 carbon atoms (lower alkenyl being presently more preferred);

(g) cycloalkylene and cycloalkenylene of 3 through 18 carbon atoms each (cyclohexyl being presently more preferred); and (h) heterocyclic Pings containing four through eight atoms per ring at least one half of which per ring are carbon atoms (six membered heterocyclic rings containing nitrogen and optionally also oxygen being more preferred).

The term "lower" as used herein refers to a designated radical that contains less than seven carbon atoms.

The term "aryl" (including usage either as a suffix as in "alkaryl" or the like, or as a prefix in the abbreviated form "ar-" as in "aralkylene" or the like) denotes an aromatic monovalent hydrocarbon radical.

An aryl radical can be substituted. Examples of substituents include halo (chloro preferred), amino (primary amines preferred), amido (primary amide groups preferred), nitro ($-NO_2$), carboxyl ($-COOH$), salts of carboxylic acids (such as $-COOM$, where M is preferably an alkali metal or ammonium), carboxylic acid ester (such as $-COOR$ where R is preferably a lower alkyl radical), and hydroxyl ($-OH$).

The alkyl and alkenyl radicals of group (e) and (f) (above) can, if desired, each optionally be substituted with substituents, such as those substituents illustratively identified above for substituted aryl moieties. Also, if desired, an alkyl or alkenyl radical can be interrupted by (that is, can include) at least one ether oxygen (oxy) or sulfur (mercapto), but preferably such an interrupted radical contains only one such oxy or mercapto component per radical.

The term "heterocyclic ring" is used herein in the conventional sense to designate a closed ring structure in which at least one of the atoms of the ring is an element other than carbon, such as oxygen, sulfur, nitrogen, or the like. A heterocyclic ring radical is in effect derived from a heterocyclic compound. Examples of suitable heterocyclic compounds include indole, pyrrole, isoindole, indolazine, furan, benzofuran, pyridazine, triazole, thiazole, oxazole, pyrazole, isoxazole, isothiazole, thiophene, pyridine, purine, indoline and the like. A heterocyclic radical can, if desired, be substituted with substituents such as those substituents illustratively identified above for substituted aryl moieties.

When a radical is substituted as indicated above, the radical preferably contains no more than two substituents and also the radical has no more than one substituent per carbon atom.

In compounds of Formula (4), preferably $R_1$ is phenyl, and preferably $R_2$ is an aromatic group-containing radical containing a total of from 6 through 18 carbon atoms (more preferably $R_2$ is a phenyl-containing group).

If on the one hand, in a compound of Formula (4), $R_1$ is hydrogen, then there is no asymmetric center and also there is no purpose in using such a compound to make a glycine derivative which is optically inactive. If, on the other hand, in a compound of Formula (4), $R_1$ is excessively large (that is, if, for example, $R_1$ is substantially larger than any radical indicated above among the preferred group of radicals identified for $R_1$ and $R_2$), then the reaction rate in the presence of the lipase is undesirably reduced and may even become negligible.

Most preferably, $R_2$ is phenyl. Certain substitutes for $R_2$, such as, for example, phenoxymenthyl appear to markedly reduce the rate of racemization in the presence of the lipase. In general, the steric effect of the $R_1$ substituent is dominant, and the electronic effect of the $R_2$ substituent is dominant in terms of influence upon rates of racemization and ring opening.

The lipase enzymes that are useful in the practice of this invention are methanolytically active lipase enzymes which, in a solvent medium and in the presence of a compound of Formula (4) and methanol, function to enantioselectively solvolyze such compound, thereby cleaving the ring structure of the Formula (4) compound between the 1 and 2 positions and also converting the carboxyl group at the 5 position into a terminal methyl ester of Formulas (5A) and (5B) below.

As used herein, the term "methanolytically active" refers to the fact that a lipase enzyme catalyzes an asymmetric solvolysis reaction between a Formula (4) compound and methanol in organic non-polar media and also concurrently cleaves the ring structure of the Formula (4) compound, thereby accomplishing enantioselective methanolysis of a Formula (4) compound to produce compounds of Formula (5) identified below.

Presently preferred lipases for use in this invention are the bacterial Pseudomonas lipases which characteristically produce a substantially complete conversion of a Formula (4) compound and which produce an enantiomeric excess $\underline{ee}$ of (S)-type compounds of at least about 60%. Yields of an intermediate product methyl ester of Formula (5) are characteristically at least about 50% (based on starting Formula (4) compound). These values can vary, and are believed to be particularly influenced by the particular C-4 substituent present in a given Formula (4) substrate.

Various suitable lipases are available commercially. Presently preferred Pseudomonas lipases are AK, K-10, P-30 and the like. As the Examples provided below illustrate, the Pseudomonas lipases are advantageous for purposes of the practice of this invention because they possess broad substrate specificities, because their enantioselectivity towards precursor compounds of Formula (4) is high, and because they generally display relatively high reaction rates towards compounds of Formula (4).

In this invention, the lipases are used in a non-polar organic solvent medium that also contains the methanol as well as the Formula (4) starting compound, as explained herein.

The term "non-polar solvent" or "non-polar liquid" as used herein has conventional reference to an organic liquid in which the positive and negative charges substantially coincide. Thus, a non-polar solvent does not ionize or impart electrical conductivity. Typically, non-polar solvents do not contain hydroxyl or carboxyl groups. A non-polar solvent suitable for use in the present invention is miscible at least in part with methanol and also is at least a partial solvent for the Formula (4) compound and the lipase at the respective concentrations that are employed in a given contacting procedure. Examples of suitable non-polar solvents include t-butyl methyl ether, methyl ether, and other ethers of lower alkyl groups; aliphatic and aromatic hydrocarbons, such as hexane, octane, cyclohexane, benzene, and the like; symmetrical halocarbons, such as carbon tetrachloride; petroleum ether; and the like. Mixtures of non-polar liquids can be used. Conveniently, the non-polar solvents used are liquids under the conditions of contacting.

Some water optionally can be and sometimes preferably is present in the non-polar liquid medium; however, it is preferred for the amount of water, if present, to be less than about 10 weight percent based on the total weight of the liquid medium.

In the solvolysis procedure, it is preferred to employ a weight ratio of the Formula (4) compound to the crude lipase that is in the range of about 1:0.1 to about 1:2, although greater or smaller weight ratios can be employed, if desired. A presently most preferred weight ratio is in the range of about 0.5:1 to about 1:1.

In the solvolysis procedure, it is preferred to employ an equivalent molar ratio of methanol to Formula (4) compound that is in the range of about 1:1 to about 10:1, although greater or smaller molar ratios can be employed, if desired. A presently most preferred equivalent molar ratio is in the range of about 4.5:1 to about 5.5:1.

In the solvolysis step, it is convenient and preferred to employ a batch procedure where the starting concentration of the Formula (4) compound in the non-polar liquid medium is in the range of about 1 to about 10 weight percent based on total weight of precursor compound and non-polar liquid (as long as the Formula (4) compound is soluble in the non-polar solvent). The use of more than one Formula (4) compound in a given solvolysis procedure is possible, but is generally not desirable because such a mixture reduces the yields of the desired highly purified enantiomeric products of Formula (5).

The preferred Pseudomonas lipases, such as AK and P30, are remarkably stable in non-polar organic solvents when the water content is low. However, some water in an amount sufficient to provide a layer (i.e., quantity) of core water relative to the enzymes of at least about 2 to about 3 weight percent based on the total solvent medium weight is believed to be typically desirable in order to maintain the structural integrity and catalytically active conformations of the lipases.

A present convenient and preferred procedure is to first dissolve the lipase enzyme in the solvent medium with the methanol and then to add the selected Formula (4) compound thereto with stirring. After this addition is complete, a preferred batch reaction medium has the initial composition listed below in Table I:

TABLE I

ILLUSTRATIVE LIPASE CONTACTING COMPOSITION
Into each 100 ml (or about each 100 parts by
weight) of non-polar organic solvent additionally
incorporate the following materials:

| Additional Component | Approximate Presently Preferred Range of Parts by Weight (based on total parts by weight of resulting composition) |
|---|---|
| (Non-polar organic solvent) | (100) |
| Substrate of Formula (4) | 2–5 |
| Methanol | 0.5–2 |
| Pseudomonas Lipase | 2–5 |
| Water (optional) | 0.5–1 |
| (Total) | (105–113) |

During the contacting, the reaction mixture preferably is continuously stirred (i.e., agitated).

The contacting of the Formula (4) compound with methanol and lipase in the non-polar solvent medium conveniently takes place at ambient temperatures, such as at temperatures in the range of about 20° to about 60° C., with temperatures of about 40° to about 50° C. being presently preferred. However, higher or lower temperatures may be used, if desired.

Total contacting time can vary. For example, it is preferred for the Formula (4) compound to be substantially completely converted during this contacting. The time needed for complete conversion to occur depends upon many variables, such as the particular lipase and the particular Formula (4) compound used; the relative concentrations of methanol, lipase and Formula (4) compound; the contacting temperature of the liquid reaction medium; and the like. Typical contacting times are in the range of about 6 to about 240 hours, but longer and shorter contacting times may be used, if desired.

Since a principal objective of the present invention is to provide a general method for the asymmetric synthesis of natural and non-natural L-α-amino acids, it is desirable to take advantage of the apparently unique properties of a Pseudomonas lipase, such as P-30 or the like, to accomplish the asymmetric cleavage of Formula (4) compounds in organic solvent media.

In such a microenvironment, non-enzymatic hydrolysis proceeds very slowly, but the rate of enolization of the C-4 proton in a Formula (4) compound is sufficiently rapid that virtually 100% of the Formula (4) substrate compound is convertible into product. When water is used as the nucleophile in non-aqueous media, the rate of ring fission is believed to be too slow to be useful. However, the chemoselectivity and reaction rate of lipase-catalyzed reaction in non-aqueous media is alterable by using different chiral nucleophiles. It was discovered that, when methanol is used as the nucleophile, methanolysis of Formula (1) compounds proceeds at a useful rate to furnish methyl esters of N-substituted-L-α-amino acids from starting 5(4H)-oxazolones. The optical purity of the methyl ester products shown in Formula (5) is believed to be typically in the range of about 66 to about 98%.

The C-4 protons of Formula (4) compounds are easily enolized in aqueous and non-aqueous media particularly when the C-2 substituent is phenyl, for example; however, use of other C-2 substituents is believed to be practical based on present data. Moreover, the chemical reactivity of 5(4H)-oxazolones is akin to that of an activated ester, so that enzyme-catalyzed ring opening of Formula (4) compounds in accord with the process of this invention is facile and relatively easy to complete. Although compounds of Formula (4) tend to be somewhat unstable in aqueous media, especially under alkaline conditions, suitable reaction conditions such as described herein have been found under which the present enzyme catalysis occurs considerably faster than a non-enzymatic hydrolysis especially for compounds of Formula (4) which bear relatively moderate to relatively large sized substituents at position C-4.

The lipase contacting is terminated conventionally by any convenient procedure. For example, one can acidify using, for instance, a strong mineral acid such as hydrochloric acid, or one can extract with a non-polar, non-water miscible organic solvent, such as ethyl acetate. The ester product is thus isolated.

The intermediate methyl ester thus produced from a precursor of Formula (4) is characterized by the following generic racemate formula:

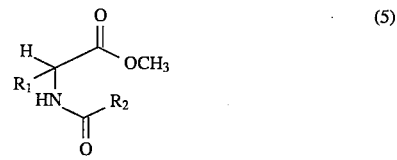

(5)

where $R_1$ and $R_2$ are as defined above in Formula (4).

An intermediate methyl ester of Formula (5) thus produced by the solvolysis is a mixture of two different optically active isomers whose respective isomeric structures are characterized by the following respective generic enantiomer formulas:

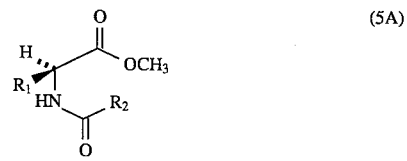

(5A)

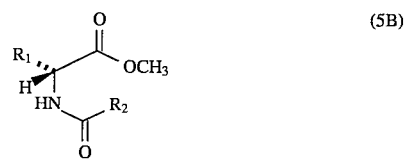

(5B)

where, in each of Formulas (5A) and (5B), $R_1$ and $R_2$ are each as defined above in relation to Formula (4). The compounds of Formula (5A) are in the (S) form and comprise typically about 80 to about 95 weight percent of the total mixture, and, correspondingly, the compounds of Formula (5B) are in the (R) form and comprise typically about 15 to about 20 weight percent of the total mixture.

A methyl ester enantiomer mixture comprising a compound of Formula (5A) and a corresponding compound of Formula (5B) is preferably purified. Any conventional purification procedure can be used. One convenient procedure employs silica gel flash chromatography where a mixture of a non-polar solvent with a polar solvent is employed, such as, for example, a mixture of hexane with ethyl acetate with the weight ratio therebetween optionally being varied for different substituents of $R_1$ and $R_2$ in Formulas (5A) and (5B).

As shown in Examples 1–15 below, a variety of different 4-substituted-2-phenyl-oxazolin-5-one derivatives of Formula (4) were exposed to the P-30 lipase in t-butyl methyl ether at 50° C. in the presence of 5 equivalents of methanol with or without 5 equivalents of water. The results are shown in Table III below.

In general, the reaction rate was somewhat faster in the presence of 5 equivalents of water, but non-enzymatic hydrolysis also occurred under these conditions resulting in a lowering of the product yield in most Examples. The enantioselectivity ranged from 66 to 95% ee and appeared to improve as the C-4 substituent in the Formula (4) starting substrate increased in size. The (S)-preferred chirality of the P-30 lipase towards the oxazolones was determined by comparing the optical rotations of several of the products to those of known N-benzoyl-L-α-amino acid methyl esters.

Also, as shown in Examples 16–30, the enantioselective properties of the three Pseudomonas lipases on several other 2-phenyl-oxazolin-5-ones of Formula (4) were evaluated. The results are shown in Table IV below. All three of the lipases employed behave similarly towards the two substrates of Examples 25–27 and Examples 28–30 of Table IV, but their actions towards 4-p-hydroxyphenyl-2-phenyl-oxazolin-5-one (Examples 22–24 of Table IV) were very different. Only the AK lipase catalyzed the methanolysis of this latter substrate with good enantioselectivity (75% ee), whereas lipases P-30 and K-10 catalyzed the solvolysis of this substrate slowly with poor enantioselectivity. For the substrate, 4-methyl-2-phenyl-oxazolin-5-one (Examples 16–21 of Table IV), it is interesting to note that, in the presence of 5 equivalents of water, both lipases P-30 and AK preferentially catalyzed the methanolysis of the (S)-enantiomer. However, in the absence of exogenous water, the enzymes changed their preferred chirality to (R) suggesting that a significant change in enzyme conformation occurs in different microenvironments. On the other hand, the lipase K-10 retained its (R)-stereochemical preference in either environment. These results demonstrate the dissimilarity of the stereochemical behavior of these bacterial lipases. However, these lipases nevertheless are useful for the practice of this invention.

To investigate whether or not further enhancement of the enantioselectivity of these enzymes could be achieved, the substituent at the C-2 position in starting Formula (4) compounds was changed. For this purpose, three substrates of Formula (4) were synthesized and exposed to the action of the bacterial lipases. The results are shown in Table V below. No marked improvement in enantioselectivity was observed. While the enantioselectivity of the 2-[4-chlorophenyl]-oxazolin-5-one (Examples 31 and 32) is very similar to that of 2-phenyl-oxazolin-5-one, the enantioselectivity for the methanolysis of 2-methyl (Example 35) and 2-trifluoromethyl-oxazolin-5-one (Examples 33 and 34) were relatively low for the lipases. However, the (S)-preferred chirality for all lipases was retained.

Thus, during solvolysis, the Pseudomonas lipases are found to possess broad substrate specificities. Their enantioselectivities towards various substrate 5(4H)-oxazolone derivatives varied, but generally are at least about 60% The enantiomeric excess in these Examples was in the range of about 66 to about 95% ee, the exact value depending upon the C-4 substituent of the Formula (4) compound.

The intermediate product methyl ester of Formula (5) is typically characterized by having an ee value in the range of about 66 to about 95% and is typically produced in a yield that is in the range of about 30 to about 91%.

(b) Hydrolysis

In the hydrolysis procedure of this invention, a dissolved enantiomeric compound mixture of Formula (5) whose composition is described above is contacted in an aqueous medium with a selected dissolved hydrolytically active protease.

The hydrolytically active protease enzymes that are useful in the practice of this invention are those which, in the presence of water, function to enantioselectivity cleave a compound of Formula (5), thereby converting the compound to the corresponding L-α-amino acid of Formula (6) identified below. As used herein, the term "hydrolytically active" refers to the fact that a protease enzyme catalyzes an asymmetric hydrolysis reaction to convert a Formula (5) compound to a Formula (6) compound in an aqueous solvent medium. A mixture of proteases with properties such as indicated herein can be used, if desired.

Various suitable proteases are available commercially. It is presently preferred to employ a protease which catalyzes this hydrolytic reaction with a high degree of enantioselectivity. Thus, the protease used should preferably should have an enantioselectivity E of at least about 100. When the precursor is a compound mixture of Formula (5), it is preferred that the protease produce a product having an enantiomeric excess (ee) of at least about 90% of L-α-amino acid, more preferably an excess of at least about 95%, and most preferably an excess of at least about 99%. Proteases which produce a yield of L-α-amino acid that is preferably in excess of about 50%, and more preferably an excess of about 85% are desired.

It has been found that surprisingly the commercially available protease enzymes prozyme 6 and protease N accommodate side chains for $R_1$ in Formula (5) compounds that are either relatively large or relatively small as well as such side chains that are of intermediate sizes. Thus, these proteases accommodate a wide variety of $R_1$ and $R_2$ substituents in Formula (5) enantiomeric mixtures. Also, these same proteases have the desired characteristics of high enantioselectivity (E), enantiomeric excess and yields. These proteases also cause catalysis to occur at commercially useful reaction rates. Hence, these proteases are presently particularly preferred for use in the practice of the present invention.

Optionally but preferably, a cosolvent comprising at least one polar solvent is present in the aqueous medium.

The term "polar solvent" or "polar liquid" as used herein has conventional reference to an organic liquid in which the positive and negative charges are separated so that the compound involved possesses an electric moment. A polar liquid can contain hydroxyl, carboxyl group, nitrile or like groups. Such a liquid achieves a dielectric constant and usually a relatively strong polarity. The polar solvent used should also preferably be water miscible.

Examples of suitable polar solvents include dioxone, tetrahydrofuran, acetonitrite, acetone, methanol and the like.

A presently most preferred polar solvent is acetonitrile. The sometimes slow reaction rate of the proteases is generally improved by the addition of a polar solvent such as acetonitrile ($CH_3CN$) to the reaction medium.

The total amount of polar solvent used in any given aqueous protease contacting procedure of this invention can vary widely. Typically, and preferably, the amount of polar liquid employed is in the range of about 1 to about 10 weight percent based on the total weight of the aqueous medium.

The amount of the enantiomeric mixtures of Formula (5) present in the aqueous contacting medium can vary. It is presently preferred to employ a starting concentration of about 1 to about 1.5 weight percent of Formula (5) substrate based on the total combined weight of Formula (5) substrate and aqueous contacting medium, although larger and smaller concentrations of Formula (5) compound can be used, if desired.

It is also preferred to employ in the aqueous medium a weight ratio of the enantiomeric compound mixture of Formula (5) to the protease that is in the range of about 1:0.5 to about 1:1. However, larger or smaller weight ratios can be employed, if desired. A presently most preferred weight ratio is in the range of about 1:0.5 to about 1:1.

Optionally but preferably, a conventional or known phosphate buffer is employed in the aqueous medium. The molar (M) amount of the buffer in the aqueous medium is preferably in the range of about 0.1 to about 0.4. A presently most preferred amount is about 0.2M. However, larger and smaller amounts of phosphate buffer can be used, if desired.

Preferably, the pH of the aqueous medium is maintained in the range of about 6 to about 9. A most preferred pH is about 6.8. However, larger and smaller pH values may be used, if desired. The pH can be adjusted with either an aqueous mineral acid such as HCl or with an aqueous alkali metal hydroxide, such as NaOH, to lower or raise, respectively, the pH to the desired value. The pH of this reaction medium is more preferably maintained at a value that is in the range of about 6.5 to about 7 with a presently most preferred pH value being about 6.8. During the contacting, the reaction mixture preferably is continuously stirred.

In the hydrolysis procedure, it is convenient and preferred to employ batch conditions. A preference is to first dissolve the protease enzyme in the aqueous contacting medium along with the optional components (phosphate buffer and organic polar cosolvent), if used. Then, the substrate of Formula (5) is added with continuous mixing. After this addition is complete, a preferred batch reaction medium has the initial composition shown below in Table II:

TABLE II

ILLUSTRATIVE PROTEASE CONTACTING COMPOSITION
Into each 100 ml (or about each 100 parts by weight) of water additionally incorporate the following materials:

| Additional Component | Approximate Presently Preferred Range of Parts by Weight (based on total parts by weight of resulting composition) |
| --- | --- |
| (water) | (100) |
| Substrate of Formula (5) | 1–1.5 |
| Protease N and/or Prozyme 6 | 1–1.5 |
| Phosphate Buffer (optional) | 1–3 |
| Polar Organic Solvent (optional) | 1–10 |
| (Total) | (104–116) |

The contacting of the Formula (5) substrate with water and protease preferably takes place at ambient temperatures, such as at a temperature in the range of about 20° to about 40° C., with a temperature in the range of about 25° to about 30° C. being more preferred. Higher and lower temperatures can be used, if desired.

Total contacting time can vary. For example, it is preferred for the Formula (5) substrate to be substantially completely converted during this contacting. The time needed for complete conversion to occur depends upon many variables, such as the particular protease and the particular Formula (5) substrate used; their respective concentrations in the aqueous medium; the presence of a polar compound such as acetonitrite; the temperature of the contacting in the liquid reaction medium; and the like. Typical contacting times are in the range of about 6 to about 36 hours, but longer and shorter contacting times may be used, if desired.

The protese contacting is terminated conventionally by any convenient procedure. For example, one can acidify the reaction system to a pH of about 2 and then isolate the acid product. The acid product precipitates out from the acidified reaction system.

The lipase and the protese enzymes can be conventionally recovered and reused, if desired. For example, in one recovery procedure, the relatively high molecular weight enzyme is recovered through retension on a membrane filter and conveniently then washed with a solvent, such as ethyl acetate. In another recovery procedure, the enzyme is immobilized and recovered as a precipitate by centrifugation. In this procedure, the supernatant can contain the product compounds.

The product α-amino acids thus produced from a Formula (5) substrate are characterized by the following generic racemate formula:

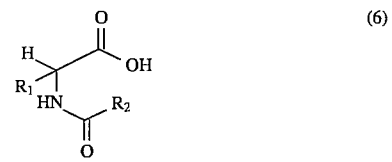

where $R_1$ and $R_2$ are as defined above in Formula (4).

The product α-amino acid thus produced by hydrolysis is a mixture of the two different optically active isomers whose respective structures are characterized by the following respective generic enantiomer formulas:

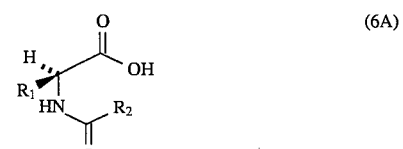

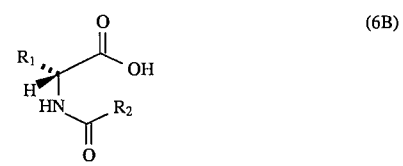

where, in each of Formula (6A) and (6B), $R_1$ and $R_2$ are as defined above relative to Formula (4). The compounds of Formula (6A) are in the (S) form and comprise typically and preferably about 100 weight percent of the total mixture (on a 100 weight percent total mixture basis) with the corresponding amount of the compounds of Formula (6B) being in the (R) form and preferably constituting less than about 1 weight percent of the total mixture.

Compounds of Formula (6) are preferably separated from the reaction mixture. Various separation procedures can be used. For example, one suitable preferred procedure is to subsequently extract the resulting aqueous mixture with a polar solvent such as ethyl acetate to remove any remaining unconverted substrate compounds of Formula (6). Two or three successive extractions with a volumetric excess (relative to the total aqueous phase volume) with ethyl acetate can be carried out after which the residual organic liquid medium can be evaporated to dryness to recover the remaining precursor Formula (5) compounds.

The resulting aqueous phase is conveniently and preferably acidified to a pH of about 2 using an aqueous mineral acid, such as 3N hydrochloric acid or the like, after which the resulting aqueous medium is extracted with a polar solvent, such as ethyl acetate, or the like. The extraction procedure can be as described above for the recovery of unconverted methyl ester. Evaporation of this extract yields the product L-α-amino acid of Formula (6).

Thus, the hydrolysis procedure of this invention converts a precursor of Formula (5) into an L-α-amino acid product using an enzyme with an enantioselectivity E of at least about 100 and with an enantiomeric excess ee of at least about 60%. Product yields are generally at least about 80% and optical purity is typically and preferably about 100%. However, in the preferred operating procedures of this invention, these values can be optimized as described.

(c) Advantages of the Two-Step Procedure

In accord with the present invention, the enzymatic asymmetric solvolysis procedure is coupled to the enzymatic kinetic resolution hydrolysis procedure to prepare L-α-amino acids of high optical purity from substrate compounds of Formula (4).

Tests and evaluations indicate that the likelihood of finding a single enzyme which would accomplish the enantioselective cleavage of all different types of Formula (4) oxazolones with high respective degrees of enantiocontrol so as to produce individual product L-α-amino acids of very high optical purity is rather remote. However, it has now been discovered that certain lipases, particularly the Pseudomonas lipases identified above, display broad specificity for catalyzing the methanolysis of Formula (4) oxazolones when methanol is used as the nucleophile in a nonpolar solvent medium. In this conversion, these lipases display a surprising capacity for enantioselectivity, as demonstrated by the following Examples. However, this enantioselectivity should be improved for commercial use.

This improvement has been achieved by the further discovery in accord with the present invention that a substantial improvement in enantioselectivity can be achieved by subjecting the product methyl esters of Formula (5) to contacting with a second enzyme, a protease, particularly prozyme 6 and protease N. In this second subsequent contacting procedure, hydrolysis is carried out in an aqueous medium. The effect is to achieve a kinetic resolution of the enantiomerically enriched product resulting from the initial methanolysis procedure. The situation may be better understood by the following Sequence:

where:

A is a compound of Formula (4) above;

B is the (S) form of the optically active methyl ester produced by the methanolysis of A achieved by the lipase;

C is the (R) form of the optically active methyl ester produced by the methanolysis of A achieved by the lipase; and D is the enriched L-α-amino acid produced by the kinetic resolution of B and C achieved by the protease.

Also in Sequence (7):

$k_1$ is the rate of lipase catalyzed methanolysis to produce B;

$k_2$ is the rate of lipase catalyzed methanolysis to produce C; and $k_3$ and $k_4$ are the respective rates of protease catalyzed hydrolysis of B and C to produce D.

In Sequence (7), $k_1$ is greater than $k_2$, and $k_3$ is much greater than $k_4$. Sequence (7) is further exemplified by the following specific reaction:

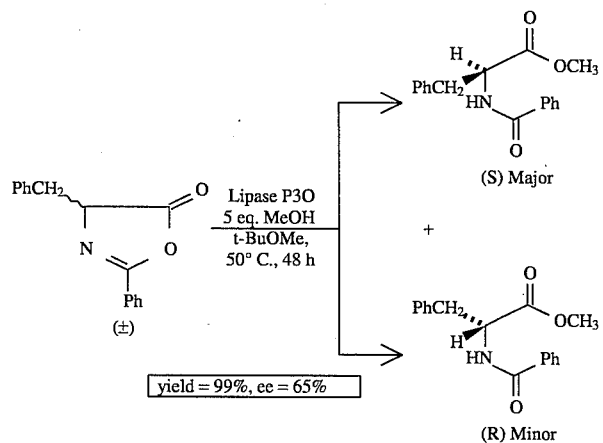

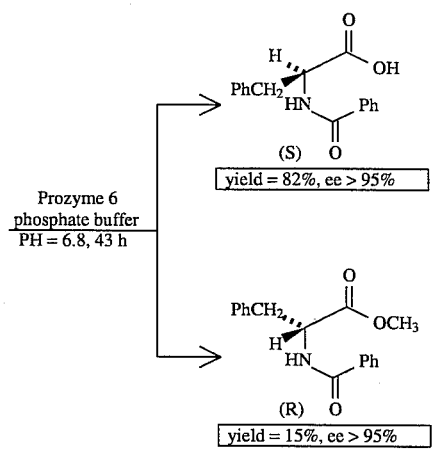

The relationship between the enantiomeric excess of the product of lipase-catalyzed methanolysis is as follows:

$$ee_o = \frac{B - C}{B + C} \qquad (9)$$

and the enantiomeric purity ee' of the final N-benzoyl-L-α-amino acids and the enantioselective value E of the protease (E=100) is governed by the following equation, where c is the extent of conversion of protease-catalyzed methyl ester hydrolysis:

$$\left[ 1 - c\left( \frac{1 + ee'}{1 + ee_o} \right) \right] = \left[ 1 - c\left( \frac{1 - ee'}{1 - ee_o} \right) \right]^E \qquad (10)$$

The accompanying FIGURE presents a plot derived from Equation (10). The plot provides a useful theoretical curve regarding the variables $ee_o$, C for fixed values of ee' (set at 0.98) and E=100. For example, assume that the product of lipase-catalyzed solvolysis of oxazolone affords an antipodal mixture with an $ee_o$ of 0.70, which is then subjected to enantioselective hydrolysis by a protease (E=100). To secure the N-benzoyl-L-α-amino acid with an ee' of ≧0.98, it is necessary to stop the reaction when C≦0.856. Equation (10) is general. Those skilled in the art will readily appreciate that plots may be obtained to relate different values of $ee_o$, ee', E and C This synergistic successive deployment of two enzymes in accord with the teachings of this invention allows the ready preparation of virtually all L-α-amino acids of high enantiopurity in yields greater than about 50%, which is an inherent advantage over all of the known and conventional resolution procedures for L-α-amino acids.

As indicated above, when the two-step procedure of the present invention is practiced, a Compound of Formula (6A) is produced in an enantiomeric excess (ee) of at least about 90%, preferably at least about 95%, and most preferably at least about 99%.

To practice the desired kinetic resolution of a mixture of the enantiomeric compounds of Formulas (5A) and (5B), it is necessary to have an enzyme that has high enantioselectivity in cleaving the methyl ester of BC (as defined in Sequence (7) which is the product of the lipase catalyzed asymmetric cleavage of compound A (as defined in Sequence (7) which is a compound of Formula (4)).

Although a lipase such as P-30 is capable of catalyzing the cleavage of the methyl ester of BC in Sequence (7) in aqueous medium, the reaction rate is believed to be too low to be of practical use. Alternatively, the use of proteases for this kinetic resolution was investigated and found to be highly satisfactory. The results shown in Table VI (Examples 36–41) clearly demonstrate that either one of two proteases is surprisingly and uniquely suited to catalyze this hydrolytic reaction with a high degree of enantioselectivity (E) of at least about 100. Both small and large amino acid side chains ($R_1$ in the Formulas 4, 5 and 6) are accommodated by the commercially available enzymes, prozyme 6 and protease N.

The two-step process of the present invention allows the lipase and the protease reactions to be coupled so that virtually any one of many natural or non-natural L-α-amino acids can be prepared in high enantiomeric excess (at least about 90%) and in high yields (at least about 50%).

EMBODIMENTS

The following Examples are presented by way of illustration only and are not in any way to be construed as limiting the scope of the invention defined in the appended claims.

Starting Materials

The following lipases were purchased from the Amano Co.: *Pseudomonas cepacia* (P-30); Pseudomonas sp. (AK and K-10); and *Aspergillus niger* (AP). Porcine pancreatic lipase (Fermilipase PL) was a product of Genencor.

Proteases prozyme 6, N and 2A were purchased from the Amano Co. α-Chymotrypsin was a product of Sigma Chemical Co.

The starting substrates were synthesized by known methods. Specifically, the 5(4H)-oxazolin-5-one derivatives were synthesized as described in Chen et al., *J. Am. Chem. Soc.*, 104, 7294–7299 (1982); Lohmer et al., *Chem. Ber.*, 113, 3706–3715 (1980); Weygand et al., *Liebigs Ann. Chem.*, 658, 128≧150 (1962); and Carter, H. E., *Org. Reactions*, 3, 198–239 (1946).

The 5(4H)-thiazolin-5-one derivatives were synthesized as described in Kjaer, A., *Acta Chem. Scand.*, 4, 347–1350 (1950); Stolowitz et al., *Anal. Biochem.*, 181, 113–119 (1989); and Barrett et al., *J. Chem. Soc.*, (C), 117–1119 (1969).

All other chemicals and solvents were of the highest quality grade available and were purchased from Aldrich Chemical Co. or Sigma Chemical Co.

Analytical Methods and Equipment $^1$H NMR spectra were recorded on a WM-200 spectrometer in deuteriochloroform with tetramethylsilane as the internal standard. Optical rotations were measured with a Perkin-Elmer model 241C polarimeter in the indicated solvents. Thin-layer chromatography (TLC) was performed on glass plates coated with a 0.25 mm of silica gel. Flash column chromatography was performed with silica gel (40 μm). All solvents were glass distilled prior to use. All combined organic extracts were dried over $MgSO_4$, filtered and evaporated to dryness under reduced pressure. For the determination of enantiomeric excess (ee), the methyl ester group was analyzed by $^1$H NMR ($CDCl_3$) in the presence of the chiral shift reagent, Eu(hfc)$_3$. All products (amino acids) were first converted into their methyl esters and then analyzed as above. The absolute configuration of the N-benzoyl-L-amino acid methyl esters and N-benzoyl-L-amino acids obtained from the enzymatic reactions were established by comparison of their optical rotations to the corresponding known derivatives prepared from L-amino acids. All yields reported herein are isolated yields.

In the following Examples, references to $R_1$ and $R_2$ refer to Formula (1) unless otherwise indicated.

EXAMPLES

EXAMPLES 1–35

Enantioselective methanolysis of 5-(4H)-oxazolone derivatives in organic solvent with lipase catalysts General procedure: To a solution of 50 mg racemic substrate in 2 ml of t-butyl methyl ether containing 5 eq. methanol (in some cases 5 eq. water was present) was added 50 mg of a crude lipase. The mixture was incubated at 50° C. until complete conversion was achieved. The progress of the reaction was monitored by TLC using the solvent system: ethyl acetate-hexane (this solvent ratio varies depending on the particular substituents for $R_1$ and $R_2$; e.g., $R_f$ value is 0.60 for N-benzoyl phenylalanine methyl ester using 1:1 ethyl acetate/hexane as the mobile phase). The crude lipase was separated from the reaction mixture by filtration, then washed with ethyl acetate. The product was purified by silica gel flash chromatography (e.g., 4:1 hexane/ ethyl acetate for N-benzoyl amino acid methyl ester, this ratio varies with different substituents for $R_2$).

The lipase P-30 catalyzed enantioselective asymmetric methanolysis of 4-substituted-2-phenyl-oxazolin-5-ones is summarized by the following equation:

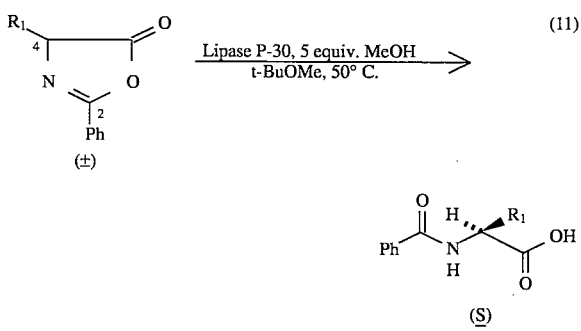

The enantioselective asymmetric methanolysis of 4-substituted-2-phenyl-oxazolin-5-ones as catalyzed by various bacterial lipases is summarized by the following equation:

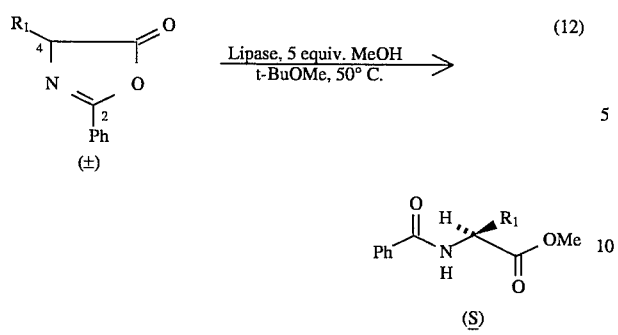

(12)

The enantioselective asymmetric methanolysis of 4-benzyl-2-substituted-oxazolin-5-ones as catalyzed by various bacterial lipases is summarized by the following equation:

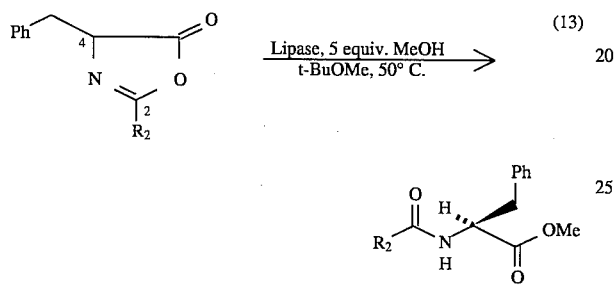

(13)

The results of the enantioselective methanolysis is summarized in Tables III, IV and V.

TABLE III

Lipase P-30 catalyzed enantioselective methanolysis of 4-substituted-2-phenyl-oxazolin-5-ones.

| Ex. No. | R1 Substituent in Formula (1) | Amount of $H_2O$ (eq.) | Time (hrs) | $[\alpha]_D$ ($CHCl_3$, c = 1) | Yield (%) | Opt. Pur. ee(%) | Opt. Conf. |
|---|---|---|---|---|---|---|---|
| 1 | $(CH_3)_2CH-$ | 5 | 130 | +30.9 | 47 | 77 | S |
| 2 | $(CH_3)_2CHCH_2-$ | 5 | 72 | +18.6 | 85 | 90 | S |
| 3 | $(CH_3)_2CHCH_2-$ | 0 | 72 | +16.1 | 82 | 78 | S |
| 4 | $CH_3SCH_2CH_2-$ | 5 | 48 | +26.0 | 31 | 82 | S |
| 5 | $CH_3SCH_2CH_2-$ | 0 | 114 | +24.8 | 56 | 71 | S |
| 6 | | 5 | 91 | +40.0 | 83 | 49 | S[1] |
| 7 | | 0 | 86 | +61.9 | 90 | 75 | S[1] |
| 8 | p-$CH_3$-phenyl-$CH_2-$ | 5 | 84 | +59.2 | 78 | 63 | S[1] |
| 9 | p-$CH_3$-phenyl-$CH_2-$ | 0 | 156 | +72.0 | 86 | 66 | S[1] |
| 10 | phenyl- | 5 | 84 | +71.7 | 46 | 75 | S[1] |
| 11 | benzyl- | 5 | 35 | +73.0 | 80 | 78 | S |
| 12 | benzyl- | 0 | 22 | +62.0 | 93 | 69 | S |
| 13 | phenyl-$CH_2CH_2-$ | 5 | 42 | +41.0 | 61 | 93 | S[1] |
| 14 | phenyl-$CH_2CH_2CH_2-$ | 5 | 72 | +33.7 | 76 | 95 | S[1] |
| 15 | phenyl-$CH_2CH_2CH_2-$ | 0 | 72 | +24.9 | 91 | 84 | S[1] |

TABLE III Footnote
[1] opt. conf. (optical conformance) presumed from circumstantial evidence and not analytically determined.

TABLE IV

Asymmetric methanolysis of 4-substituted-2-phenyl-oxazolin-5-ones catalyzed by bacterial lipases.

| Ex. No. | $R_1$ Substituent in Formula (1) | Lipase | Time (hrs) | Yield (%) | $[\alpha]_D$ (CHCl$_3$) | Opt. Pur. ee(%) | Opt. Conf. |
|---|---|---|---|---|---|---|---|
| 16 | (CH$_3$)- | AK | 69 | 76 | −0.6 | — | R |
| 17 | | AK (5 eq. H$_2$O) | 15 | 46 | +5.0 | 18 | S |
| 18 | | P-30 | 23 | 91 | −3.6 | 59 | R |
| 19 | | P-30 (5 eq. H$_2$O) | 38 | 39 | +1.8 | 50 | S |
| 20 | | K-10 | 69 | 80 | −2.2 | 13 | R |
| 21 | | K-10 (5 eq. H$_2$O) | 86 | 50 | −3.9 | 15 | R |
| 22 | p-OH-phenyl- | AK | 76 | 52 | +72.6 | 75[a] | S |
| 23 | | P-30 | 112 | 32 | +17.7 | 18[a] | S |
| 24 | | K-10 | 88 | 22 | +4.8 | 5[a] | S |
| 25 | p-OH-phenylCH$_2$— | AK | 16 | 39 | +52.0 | 61[a] | S |
| 26 | | P-30 | 66 | 40 | +60.1 | 71[a] | S |
| 27 | | K-10 | 97 | 57 | +58.5 | 69[a] | S |
| 28 | phenyl-CH$_2$SCH$_2$— | AK | 15 | 69 | −6.3 | 79 | S |
| 29 | | P-30 | 23 | 64 | −6.4 | 80 | S |
| 30 | | K-100 | 23 | 61 | −9.6 | 90 | S |

[a]The ee value is determined as the p-methoxyphenyl derivative.

TABLE V

Enzymatic enantioselective methanolysis of 4-benzyl-2-substituted-oxazolin-5-ones.

| Ex. No. | $R_2$ Substituent in Formula (1) | Enzyme | Time (hrs) | $[\alpha]$ (CHCl$_3$, c = 1) | Yield (%) | Opt. Pur. ee(%) |
|---|---|---|---|---|---|---|
| 31 | p-Cl-phenyl- | P-30 | 23 | +74.9 | 73 | 75 |
| 32 | | K-10 | 72 | +74.8 | 78 | 76 |
| 33 | CF$_3$— | P-30 | 73 | +30.9 | 31 | 39 |
| 34 | | AK | 88 | +28.7 | 58 | 30 |
| 35 | CH$_3$— | P-30 | 24 | +18.4 | 52 | 20 |

EXAMPLES 36–41

Enantioselective hydrolysis of N-benzoyl amino acid methyl esters in aqueous solvent with protease catalysts General procedure: To 50 mg of a (±)N-benzoyl amino acid methyl ester produced as described in the procedure of Examples 1–35 (above) and suspended in 4 ml of aqueous 0.2M phosphate buffer (pH 6.8), was added 50 mg of a crude protease (prozyme 6 or protease N). The mixture was stirred vigorously with a magnetic stirrer at 25° C. until approximately 50% of the substrate was transformed into product (monitored by TLC). The reaction was terminated by the addition of saturated NaHCO$_3$ and extracted with ethyl acetate (3×20 ml). Evaporation of the organic extract to dryness afforded the remaining N-benzoyl-D-amino acid methyl ester. The aqueous phase was acidified to pH 2 with 3N HCl and extracted with ethyl acetate (3×20 ml). The organic extract was evaporated to yield the product N-benzoyl-L-α-amino acid.

The protease catalyzed enantioselective hydrolysis for the kinetic resolution of the N-benzoyl-amino-acid methyl esters is summarized by the following equation:

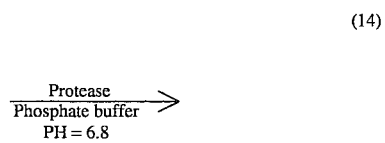

(14)

The results of the enantioselective hydrolysis are summarized in Table VI.

TABLE VI

Protease-catalyzed kinetic resolution of N-benzoyl-amino acid methyl esters.

| Ex. No. | $R_1$ | Enzyme | Time (h) | Substrate (rem) Yield (%) | ee (%) | Product Yield (%) | ee (%) | Conversion (%) | E |
|---|---|---|---|---|---|---|---|---|---|
| 36 | Me | Prozyme 6 | 6 | 42 | 95 | 43 | 85 | 52 | 45 |
| 37 |  | Protease N | 6 | 43 | 95 | 40 | 95 | 50 | >100 |
| 38 | $Me_2CH$ | Prozyme 6 | 6 | 41 | 95 | 43 | 95 | 50 | >100 |
| 39 |  | Protease N | 6 | 42 | 95 | 39 | 95 | 50 | >100 |
| 40 | $PhCH_2$ | Prozyme 6 | 30 | 31 | 100 | 44 | 100 | 50 | >100 |
| 41 |  | Protease N | 21 | 43 | 100 | 37 | 100 | 50 | >100 |

EXAMPLE 42

Enantioselective solvolysis followed by kinetic resolution procedure

The reaction mixture contained 250 mg of (±)-4-benzyl-2-phenyloxazolin-5-one and 250 mg of crude lipase P-30 in 20 ml of t-butyl methyl ether. The mixture was incubated at 50° C. for 48 hours. The lipase P-30 was separated from the reaction mixture by filtration and washed with ethyl acetate. The combined organic layer was concentrated to dryness under reduced pressure to yield 280 mg of N-benzoyl-L-phenylalanine methyl ester (99% yield; 65% ee).

A suspension of 280 mg of the above residue and 280 mg of crude prozyme 6 in 20 ml of 0.2M phosphate buffer (pH 6.8) was stirred vigorously at room temperature for 43 hours. The reaction mixture was terminated by the addition of $NaHCO_3$ and then extracted with ethyl acetate (3×30 ml). Concentration of the combined organic layers gave the remaining substrate, 43 mg (15.3%). The aqueous phase was acidified to pH 2 with 3N HCl and extracted with ethyl acetate (3×30 ml). The combined organic layers were concentrated to dryness to give 220 mg of N-benzoyl-L-phenylalanine (82%) (ee>95%), 82.1%, $[\alpha]_D=-30°$ (c, 1.0, $CH_3OH$).

Those skilled in the art will readily appreciate that other and further modifications, changes, variations and the like may be made in the details and aspects of the present disclosure without departing from the spirit and scope of this invention.

What is claimed is:

1. An enzymatic process for preparing an L-α-amino acid which comprises the sequential steps of:

(A) contacting in a non-polar solvent a precursor of said amino acid that is selected from 4-substituted-5(4H)-oxazolones with a catalytically effective amount of a methanolytically active lipase in the presence of methanol so as to enantioselectively solvolyze said precursor and produce the methyl ester of said amino acid, said precursor has the generic formula:

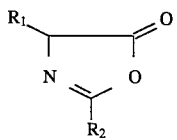

where $R_2$ is phenyl and $R_1$ is an organo moiety that is substantially inert in the presence of the methanolytically active lipase and is selected from the group of radicals consisting of:

(a) aryl of 6 through 12 carbon atoms;
   (b) alkaryl of 6 through 18 carbon atoms;
   (c) aralkylene of 7 through 18 carbon atoms;
   (d) aralkenylene of 8 through 18 carbon atoms;
   (e) alkyl of 1 through 17 carbon atoms;
   (f) alkenyl of 1 through 17 carbon atoms;
   (g) cycloalkylene and cycloalkenylene of 3 through 18 carbon atoms each; and
   (h) heterocyclic rings containing 4 through 8 atoms per ring, at least one half of which per ring are carbon atoms; and (B) contacting in an aqueous medium said methyl ester with a catalytically effective amount of a hydrolytically active protease which has an enantioselectivity relative to said methyl ester in water of at least about 100 so as to enantioselectively cleave said methyl ester, and produce said L-α-amino acid in an optical purity of at least about 90 percent.

2. The process of claim 1 wherein said lipase is at least one Pseudomonas lipase.

3. The process of claim 2 wherein said Pseudomonas lipase is selected from the group consisting of AK, K-10 and P-30.

4. The process of claim 1 wherein said protease is selected from the group consisting of prozyme 6 and protease N.

5. The process of claim 1 wherein said precursor is a 4-substituted-2-substituted-oxazolin-5-one.

6. The process of claim 1 wherein said methyl ester is a mixture of two different optically active isomers, one of said isomers being in the (S) form and has the following generic formula:

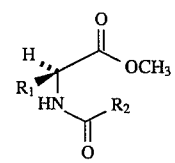

wherein:
   $R_1$ is an organo moiety that is substantially inert in the presence of a methanolytically active lipase and $R_2$ is phenyl; and where, in said mixture, the enantiomeric excess of said isomer in said (S) form is at least about 60 percent.

7. The process of claim 1 wherein said L-α-amino acid has the generic formula:

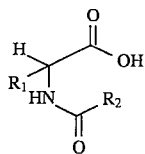

wherein:

R₁ is an organo moiety that is substantially inert in the presence of a methanolytically active lipase and $R_2$ is phenyl; and where the optical purity of said L-α-amino acid is at least about 95 percent.

8. The process of claim 7 wherein said precursor is a 4-substituted-2-phenyl-oxazolin-5-one, said amino acid methyl ester is an N-benzoyl-L-α-amino acid methyl ester, and said L-α-amino acid is an N-benzoyl-L-α-amino acid.

9. The process of claim 8 wherein said L-α-amino acid is produced in a yield greater than about 50 percent and has an optical purity of at least about 99%.

10. The process of claim 1 wherein said contacting in a non-polar solvent is carried out batch-wise in a reaction mixture having the following composition: In each 100 parts by weight of non-polar organic solvent, there is additionally incorporated:

about 2 to about 5 parts by weight of said precursor; and about 0.5 to about 2 parts by weight of said methanol.

11. The process of claim 10 wherein said reaction mixture further additionally incorporates about 0.5 to about 1 part by weight of water.

12. The process of claim 1 wherein said contacting in an aqueous medium is carried out batch-wise in a reaction mixture having the following composition: In each 100 parts by weight of water, there is additionally incorporated:

about 1 to about 1.5 parts by weight of said methyl ester; and about 1 to about 1.5 parts by weight of said protease.

13. The process of claim 12 wherein said reaction mixture further additionally incorporates about 1 to about three parts by weight of phosphate buffer.

14. The process of claim 12 wherein said reaction mixture further additionally incorporates about 1 to about 10 parts by weight of polar organic solvent.

* * * * *